United States Patent
Jalisi et al.

(10) Patent No.: US 6,203,505 B1
(45) Date of Patent: *Mar. 20, 2001

(54) GUIDEWIRES HAVING A VAPOR DEPOSITED PRIMER COAT

(75) Inventors: Marc Mehrzad Jalisi; Emmanuel C. Biagtan, both of Temecula, CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/092,229

(22) Filed: Jun. 5, 1998

(51) Int. Cl.$^7$ .............................. A61B 5/00; A61M 25/00
(52) U.S. Cl. ................................................ 600/585
(58) Field of Search ..................... 600/585, 347, 600/393; 607/122; 428/380; 604/265

(56) References Cited

U.S. PATENT DOCUMENTS

| | | | |
|---|---|---|---|
| 4,952,357 | 8/1990 | Euteneuer | 264/129 |
| 5,084,151 | 1/1992 | Vallana et al. | 204/192.11 |
| 5,272,012 | 12/1993 | Opolski | 428/423.1 |
| 5,295,978 | 3/1994 | Fan et al. | 604/265 |
| 5,356,433 | 10/1994 | Rowland et al. | 623/11 |
| 5,387,247 | 2/1995 | Vallana et al. | 623/66 |
| 5,443,455 | 8/1995 | Hergenrother et al. | 428/380 |
| 5,455,072 | 10/1995 | Bension et al. | 427/255.7 |
| 5,477,864 | 12/1995 | Davidson | 128/772 |
| 5,506,059 | 4/1996 | Robbins et al. | 428/457 |
| 5,520,664 | 5/1996 | Bricault, Jr. et al. | 604/265 |
| 5,552,027 | 9/1996 | Birkle et al. | 204/290 |
| 5,562,730 | 10/1996 | Davidson | 623/3 |
| 5,588,443 | 12/1996 | Davidson | 128/772 |
| 5,607,463 | 3/1997 | Schwartz et al. | 623/1 |
| 5,630,840 | 5/1997 | Mayer | 623/1 |
| 5,647,858 | 7/1997 | Davidson | 604/264 |
| 5,648,127 | 7/1997 | Turchan et al. | 627/596 |
| 5,722,424 | * 3/1998 | Engelson | 600/585 |
| 5,735,896 | 4/1998 | Amon et al. | 623/11 |
| 5,750,206 | 5/1998 | Hergenrother et al. | 427/490 |
| 5,924,998 | * 7/1999 | Cornelius et al. | 600/585 |
| 5,984,878 | * 11/1999 | Engelson | 600/585 |

FOREIGN PATENT DOCUMENTS

| | | | |
|---|---|---|---|
| 4112936A1 | 4/1991 | (DE) | A61N/1/05 |
| 0747069A2 | 6/1996 | (EP) | A61L/29/00 |
| 0747069A3 | 6/1996 | (EP) | A61L/29/00 |
| 0769306A2 | 9/1996 | (EP) | A61M/25/01 |
| 0769306A3 | 9/1996 | (EP) | A61M/25/01 |

OTHER PUBLICATIONS

International Search Report from related PCT Application No. PCT/US99/11903.

Alexis T. Bell, "Review of Lecture on Plasma Polymerization and Structure of Plasma Films and Oils", *The First Annual International Conference of Plasma Chemistry and Technology*, Nov. 14–17, 1982.

* cited by examiner

Primary Examiner—Max Hindenburg
Assistant Examiner—Brian Szmal
(74) Attorney, Agent, or Firm—Heller, Ehrman, White & McAuliffe LLP

(57) ABSTRACT

An intraluminal device having an adhesive primer coat formed of a carbonaceous material and a lubricious top coat of a hydrophilic polymeric material. The invention also comprises the methods of making such intraluminal devices. The primer coat of the invention may comprise pure carbon, or a carbon based material such as a polymer. Preferably, the primer coat has a thickness of about 0.1 to about 2 $\mu$m. In a presently preferred embodiment, the primer coat is applied using chemical vapor deposition (CVD), but in certain embodiments, physical vapor deposition (PVD) may be suitable. The deposited primer coat forms an effective substrate for adhesion of the hydrophilic polymer top coat.

10 Claims, 2 Drawing Sheets

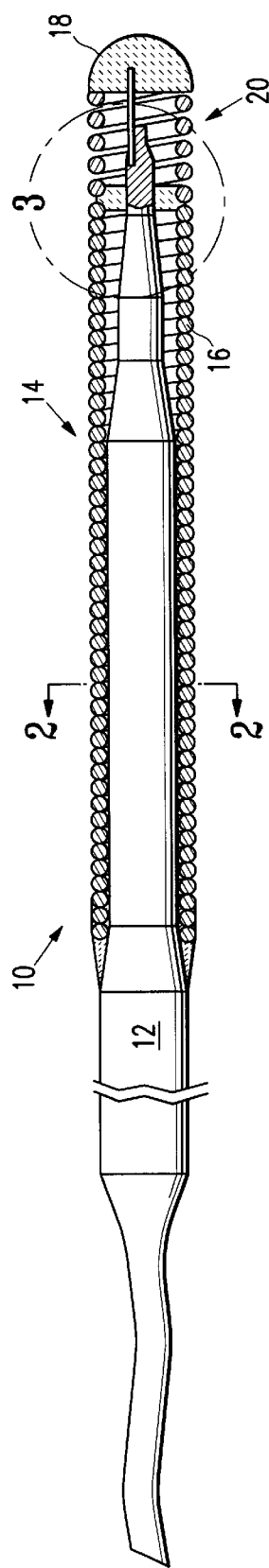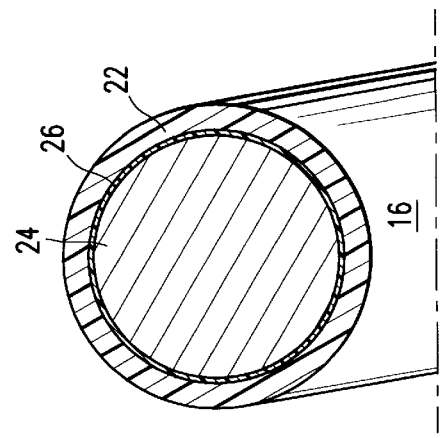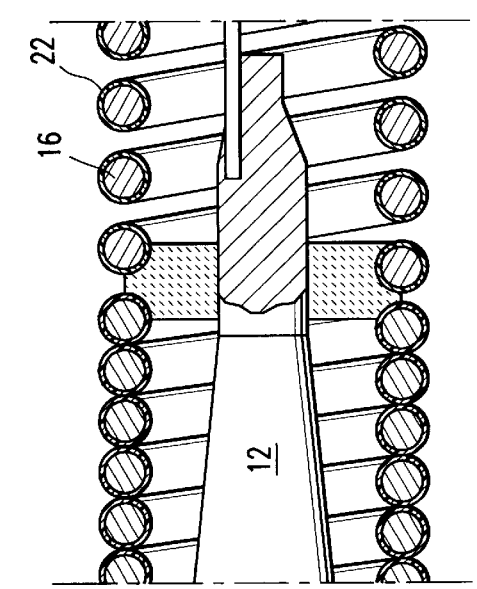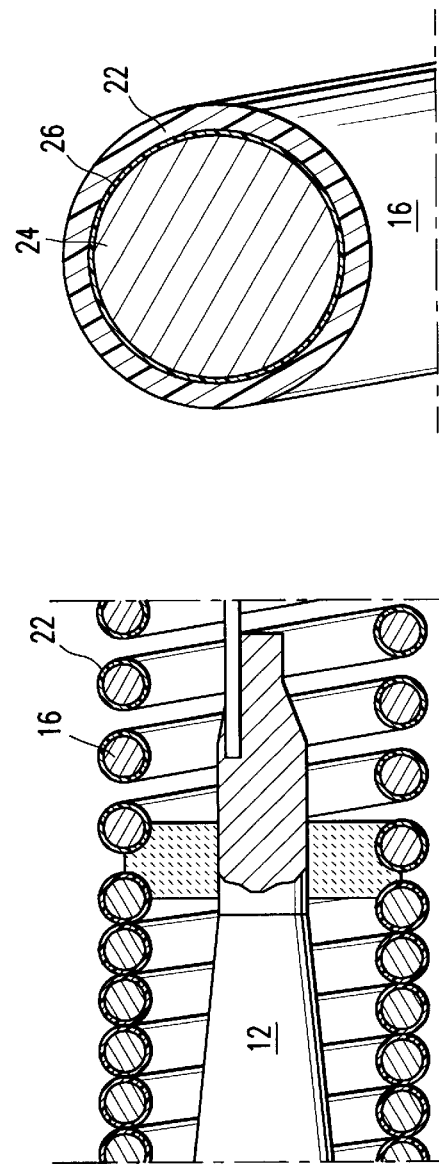

GUIDEWIRES HAVING A VAPOR DEPOSITED PRIMER COAT

BACKGROUND OF THE INVENTION

This invention is directed to the field of elongated intraluminal devices having lubricious coatings, and, in particular, to a guidewire having a thin carbonaceous primer coat and a hydrophilic polymer top coat.

In a typical coronary procedure a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. There are two basic techniques for advancing a guidewire into the desired location within the patient's coronary anatomy, the first is a preload technique which is used primarily for over-the-wire (OTW) devices and the bare wire technique which is used primarily for rail type systems. With the preload technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g. a lesion to be dilated or a dilated region where a stent is to be deployed. The catheter, which is slidably mounted onto the guidewire, is advanced out of the guiding catheter into the patient's coronary anatomy over the previously introduced guidewire until the operative portion of the intravascular device, e.g. the balloon of a dilatation or a stent delivery catheter, is properly positioned across the arterial location. Once the catheter is in position with the operative means located within the desired arterial location, the interventional procedure is performed. The catheter can then be removed from the patient over the guidewire. Usually, the guidewire is left in place for a period of time after the procedure is completed to ensure reaccess to the arterial location if it is necessary. For example, in the event of arterial blockage due to dissected lining collapse, a rapid exchange type perfusion balloon catheter such as described and claimed in U.S. Pat. No. 5,516,336 (McInnes et al.), can be advanced over the in-place guidewire so that the balloon can be inflated to open up the arterial passageway and allow blood to perfuse through the distal section of the catheter to a distal location until the dissection is reattached to the arterial wall by natural healing.

With the bare wire technique, the guidewire is first advanced by itself through the guiding catheter until the distal tip of the guidewire extends beyond the arterial location where the procedure is to be performed. Then a rail type catheter, such as described in U.S. Pat. No. 5,061,395 (Yock) and the previously discussed McInnes et al. which are incorporated herein by reference, is mounted onto the proximal portion of the guidewire which extends out of the proximal end of the guiding catheter which is outside of the patient. The catheter is advanced over the catheter, while the position of the guidewire is fixed, until the operative means on the rail type catheter is disposed within the arterial location where the procedure is to be performed. After the procedure the intravascular device may be withdrawn from the patient over the guidewire or the guidewire advanced further within the coronary anatomy for an additional procedure.

Conventional guidewires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapeable member, which may be the distal extremity of the core member or a separate shaping ribbon which is secured to the distal extremity of the core member extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson et al.) which are hereby incorporated herein in their entirety by reference thereto.

Guidewires have been the subject of continual improvement. One direction of improvement has centered on reducing the surface friction of the guidewire to facilitate relative movement between the guidewire and a guiding catheter or a dilatation catheter within a patient's body lumen. Much of the innovation has centered on laminating low friction, polymeric materials onto the surface of the guidewire. However, it has proven difficult to obtain a tenacious bond between the lubricious polymer coating and the material of the guidewire. Further, achieving a uniform coat of polymer over the helical shapeable distal tip of most guidewires presents several difficulties. For example, bridging of the coat material between adjacent coils interferes with the designed flexibility of the distal tip and thereby effects performance of the guidewire.

In addition to guidewires, many intraluminal devices can benefit from a lubricious surface to facilitate insertion and guidance to the desired intraluminal destination. Reducing friction also minimizes luminal trauma caused by insertion of these devices, particularly in blood vessels such as coronary arteries. As with guidewires, much has been done with the prior art lubricious polymeric coatings to produce intraluminal devices having low friction surfaces. However, a number of drawbacks are associated with the use of polymeric coatings. Providing such devices with a uniform and tenacious coating is technically difficult and correspondingly expensive.

There remains a need for intraluminal devices having a lubricious polymeric coating which is thin and which is strongly adhered to the device. Further, there is a need for a process of applying such lubricious polymeric coatings in a repeatable, uniform and cost effective manner. This invention satisfies these and other needs.

SUMMARY OF THE INVENTION

This invention comprises an intraluminal device having a vapor deposited primer coat formed of a carbonaceous material and a lubricious top coat of a hydrophilic polymeric material. The invention also comprises the methods of making such intraluminal devices.

The vapor deposited primer coat of the invention may comprise substantially pure carbon, or a carbon-based material such as plasma polymerized hydrocarbons, polyurethane, or nylon, and preferably has a thickness of about 0.1 to about 2 μm. A variety of carbonaceous source materials may be used to form the primer coat depending on the composition of the primer coat and the coating method used. The primer coat is applied to the surface of the intraluminal device using chemical vapor deposition (CVD), or in certain embodiments as discussed below, physical vapor deposition (PVD). The deposited primer coat forms an effective substrate for adhesion of a later applied hydrophilic polymer top coat. The hydrophilic polymer top coat may be applied by a variety of methods, including CVD, PVD, dipping, spraying and the like.

In a presently preferred embodiment of the invention, the primer coat and the hydrophilic top coat are applied to the surface of a distal tip coil of a guidewire. The use of vapor deposition provides a thin primer coat which provides uniform coverage of the helical coil. In a presently preferred embodiment of the invention, at least a stretched section of the coil are coated such that the adjacent turns of the coated coils do not touch one another. A thicker, less uniform primer coat would likely bridge the adjacent coils, or significantly increase the diameter of the coils so that bridging would likely result in the lubricious top coat, which can interfere with guidewire performance.

The deposited primer coat of the invention has superior adhesion to the base material of an intraluminal device, and provides improved adhesion between a hydrophilic top coat and the device. Additionally, the deposited primer coat does not bridge the adjacent turns of guidewire tip coils, and does not significantly increase the thickness of the coating on the device. These and other advantages of the invention will become more apparent from the following detailed description and accompanying exemplary drawings.

BRIEF DESCRIPTION OF THE DRAWINGS

FIG. 1 illustrates guidewire of the invention with a shapeable coil tip and a distal portion having an adhesive primer coat and a hydrophilic polymer top coat.

FIG. 2 is a cross section of the intermediate coil of the guidewire of FIG. 1.

FIG. 3 is a sectional detail of the shapeable coil showing the hydrophilic polymer top coat.

FIG. 4 is a further detail of FIG. 3, showing the hydrophilic polymer top coat and the adhesive primer coat.

DETAILED DESCRIPTION OF THE INVENTION

Figure 5:
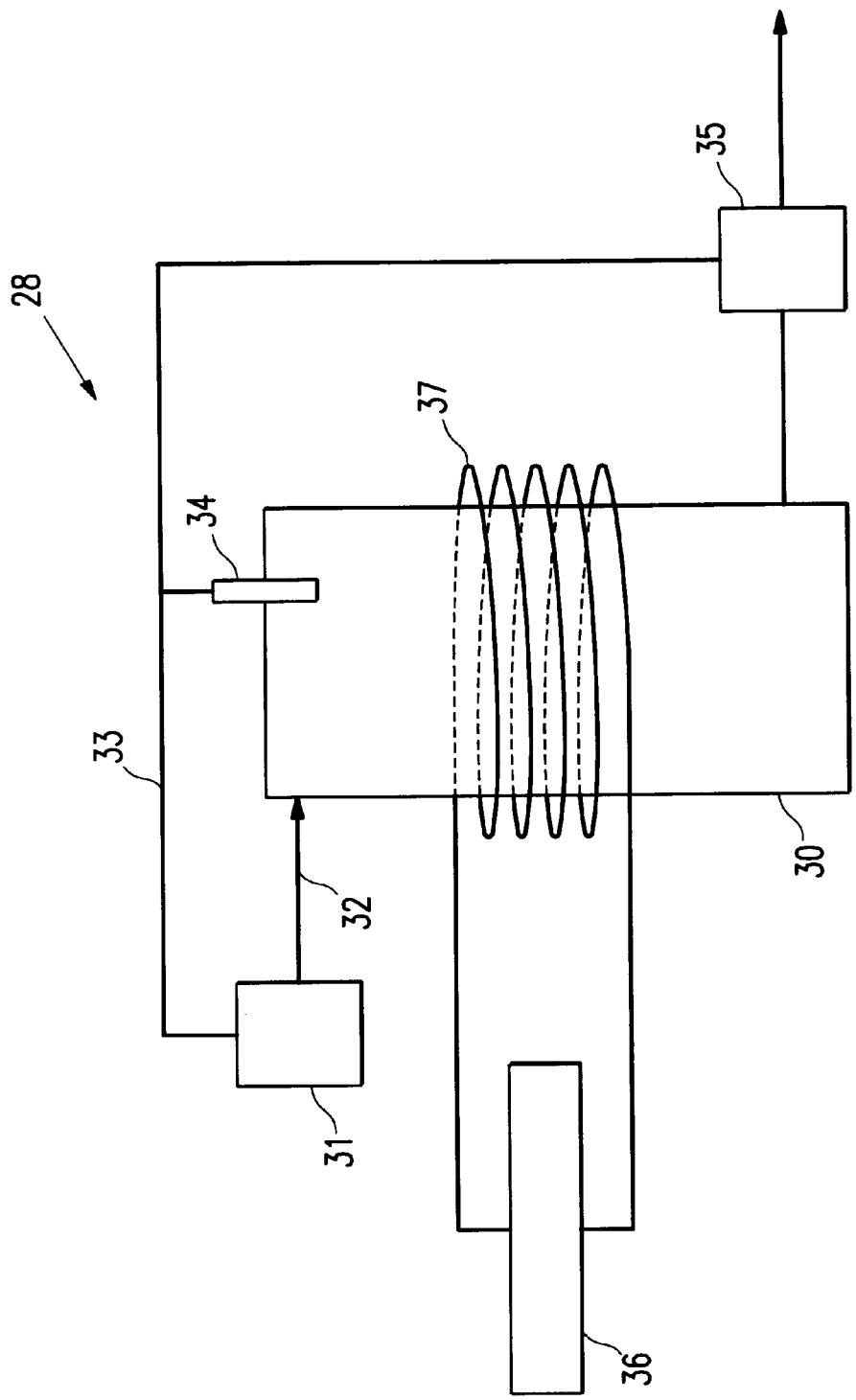
FIG. 5 is schematic diagram of a CVD apparatus suitable for the practice of this invention.

FIGS. 1–4 illustrate a guidewire 10 having features of this invention that generally include an elongated core member 12 and a distal tip 14 having a thin carbonaceous primer coat and a hydrophilic top coat on at least a portion thereof. The distal tip 14, which may be shaped or shapeable, comprises a flexible helical coil 16 and a rounded member 18 on the distal extremity, preferably formed by a solder plug securing helical coil 16 to core member 12. FIG. 3 shows a detail of the distal portion 20 of the helical coil 16 which has a uniform hydrophilic polymer coating 22. Various portions of the guidewire may be coated as desired. In a presently preferred embodiment, the distal 30 cm of guidewire 10 is coated, which includes the flexible helical coil 16 and a portion of the core member proximal to the intermediate coils. In other embodiments, only the coils 16 or only a distal portion of the coils, such as the distal 3 cm coils, may be coated, depending on the desired guidewire characteristics.

FIG. 4 is a further sectional detail of helical coil 16, showing the base material 24 of the coil, adhesive primer coat 26 and hydrophilic polymer top coat 22. Generally, base material 24 of guidewire 10 is stainless steel, but it may comprise a shape memory material such as nickel-titanium alloys or other materials. Primer coat 26 is either substantially pure carbon, or a carbon-based material.

In the embodiment in which the primer coat 26 is substantially pure carbon, a variety of source materials may be used to form the carbon primer coat, including graphite and pyrolytic carbon. The presently preferred coating method for applying a substantially pure carbon primer coating 26 from a graphite or pyrolytic carbon source is physical vapor deposition.

The presently preferred coating method for applying a carbon-based primer coating 26 is chemical vapor deposition. It should be understood that the carbon-based primer coating 26 applied by CVD comprises a plasma polymerized coating, so that the resulting polymer comprises an amorphous structure having groups in the structure other than the monomer groups of the source materials. For example, plasma polymerized polyethylene may include a variety of functional groups, such as vinyl, in addition to the methylene groups. The presently preferred carbon-based primer coating 26 is plasma polymerized nylon or plasma polymerized polyethylene. However, a variety of suitable carbon-based polymeric primer coatings may be used including plasma polymerized polypropylene, plasma polymerized polyurethane, and the like. A variety of suitable carbon based source materials may be used to form the carbon-based primer coating 26. For example, vapor reactants having the carbonyl and amine functional groups characteristic of nylon, such as adipic acid and hexanediamine, may be used to form a plasma polymerized nylon primer coat. Additionally, hydrocarbons such as methane, ethane, hexane and the like, may be used as source materials. Primer coat 26 is very thin, generally about 0.1 to about 2 μm depending on the type of material.

Any suitable hydrophilic polymer may be used as top coat 22, including poly(N-vinylpyrrolidone) (PVP), polyethylene oxide (PEO), Hydro Gel™, methacrylates and the like. Generally, the thickness of top coat 22 is about 0.0025 mm (0.1 mil) to about 0.015 mm (0.5 mil), but may vary depending on the application. Any suitable means of applying top coat 22 may be employed, including vapor deposition, dipping, spraying and the like.

The length of the guidewire 10 may be about 160 cm to about 310 cm. The OD of the guidewire and distal tip coil is about 0.025 cm to about 0.05 cm. The distal tip coil is formed from wire having a diameter of about 0.002 in (0.05 mm) to about 0.0055 in (0.14 mm). The spacing between adjacent turns of the helically wound coils varies along the length of the device, from substantially stacked coils having substantially space between adjacent coils, to stretched coils having a spacing of about 15% to about 30% of the wire diameter.

CVD typically involves vaporized compounds flowing over a substrate. A plasma can be generated via RF energy or the like to activate the deposition reactions. The reaction of the compounds in the plasma state and at the substrate surface results in a film coating. CVD should be performed at low pressures to enhance the quality of the coating. The use of a CVD process allows the application of very thin, uniform and repeatable primer coats, without causing bridging between adjacent coils on the guidewire.

FIG. 5 is a schematic diagram of a suitable CVD apparatus 28, having a reaction chamber 30, gas/vapor source 31, gas/vapor inlet 32, an electronic pressure regulator system 33, a pressure sensor, 34, a vacuum pump 35, a RF power supply and regulator 36, and RF induction coils 37 around the outside of the chamber. As an alternative to induction coils, plasma can be generated via capacitor plates (not shown), typically located inside the chamber 30. Before deposition of the primer coat 26, the guidewire is typically cleaned using well known procedures, such as washing with a solvent such as 1,1,1, trichloroethane, or exposure to ultrasonication or the plasma gas in the CVD chamber. Generally, the guidewire is suitably masked and placed in reaction chamber 30. A nonreactive gas such as argon is used to purge the chamber atmosphere and the pressure is reduced to less than about 50 mtorr. RF power supply 36 and induction coils 37 are used to generate a plasma from the chamber gas. Desired gases or vapors are introduced through inlets 32, which in the presence of the plasma, polymerize and deposit on the substrate. The reaction is allowed to continue until a sufficiently thick layer of primer coat is deposited, then the plasma is turned off and the chamber purged again with nonreactive gas. In general, the plasma power is about 5 to 50 Watts and the gas/vapor flow is less than about 20 sccm. Under these parameters, a suitable primer coat is applied in about 1 to 10 minutes. A plasma polymerized polyethylene coating was applied using hexane vapor as a source material, at a power of 50 W and a flow rate of 5 sccm for 10 minutes.

The primer coat 26 may be applied using physical vapor deposition (PVD). In general, PVD involves generation of the coating, transport of the coating to the substrate and growth of the coating on 10 the substrate. Generation of the coating may be achieved either by evaporation or sputtering. In evaporative schemes, thermal energy from resistance, induction, electron-beam or laser beam sources is used to vaporize the coating. Sputtering, on the other hand uses plasma ions generated by direct current or radio frequency to energize and eject species of the coating material towards the substrate. Generating species with greater energies can improve adhesion with the substrate. Transport of the vaporized coating generally depends on the partial pressure of the vaporized coating; for example molecular flow occurs at low partial pressures while viscous flow occurs at higher partial pressures. Depending on the technique, the substrate may also be biased. Finally, growth of the coating depends on the energy of the vaporized coating and substrate temperature. One of skill in the art will be able to tailor the conditions to the type of coating being applied and the substrate material.

While the invention has been described herein primarily with reference to presently preferred embodiments comprising an adhesive primer coat applied to a guidewire through vapor deposition, various modifications and improvements can be made to the invention without departing from the scope thereof. For example, while the carbon-based primer coatings were primarily described as a CVD polymerized coating, PVD may also be used to apply the primer coat. The coatings may be applied to a variety of intraluminal products including electrophysiology devices, atherectomy catheters, stents and the like without departing from the scope thereof.

What is claimed is:

1. A guidewire comprising an elongated core member and a flexible helical coil disposed about a distal end of the core member, the flexible helical coil having a primer coat formed of a carbonaceous material vapor deposited on at least a portion thereof, and a hydrophilic polymer top coat on at least a portion of the primer coat.

2. The guidewire of claim 1, wherein the primer coat has a uniform thickness of not more than about 2 $\mu$m.

3. The guidewire of claim 1, wherein the primer coat is selected from the group consisting of carbon, plasma polymerized nylon, plasma polymerized polyurethane, plasma polymerized polyethylene, and plasma polymerized hydrocarbons.

4. The guidewire of claim 1, wherein the top coat is selected from the group consisting of poly(N-vinylpyrrolidone), and polyethylene oxide.

5. The guidewire of claim 1, wherein the top coat has a thickness of about 0.0025 mm to about 0.015 mm.

6. The guidewire of claim 1, wherein adjacent turns of the flexible helical coil are individually coated so that the primer coat and the top coat do not bridge the adjacent turns of the coil.

7. A method of making a guidewire having a lubricious surface, comprising applying a primer coat formed on a carbonaceous material on at least a portion of a flexible helical coil disposed about a distal end of an elongate core member of the guidewire by vapor deposition, and then applying a hydrophilic polymeric coat on at least a portion of the primer coat.

8. The method of claim 7, wherein the primer coat is applied by chemical vapor deposition.

9. The method of claim 8, wherein the primer coat is applied until the primer coat is about 0.1 $\mu$m to about 2 $\mu$m thick.

10. The method of claim 7, wherein the primer coat is applied by physical vapor deposition.

\* \* \* \* \*